United States Patent [19]
Gray et al.

[11] Patent Number: 5,478,496
[45] Date of Patent: Dec. 26, 1995

[54] MEDIA CONTAINING THIAZOLE DERIVATIVES AND THIADIAZOLE DERIVATIVES AND HAVING A SMECTIC LIQUID-CRYSTALLINE PHASE

[75] Inventors: George W. Gray, Cottingham; Richard M. Scrowston, Walkington; Kenneth J. Toyne; David Lacey, both of Hull; Adam Jackson, Swanland, all of Great Britain; Joachim Krause, Dieburg, Germany; Eike Poetsch, Mühltal, Germany; Thomas Geelhaar, Mainz; Georg Weber, Erzhausen, Germany; Andreas Wächtler, Griesheim, Germany

[73] Assignee: Merck Patent Gesellschaft mit Beschrankter Haftung, Darmstadt, Germany

[21] Appl. No.: 983,262

[22] Filed: Nov. 30, 1992

Related U.S. Application Data

[63] Continuation of Ser. No. 299,917, filed as PCT/EP88/00279, Apr. 5, 1988, abandoned.

[30] Foreign Application Priority Data

Apr. 16, 1987 [DE] Germany ............... 37 12 995.3
Sep. 15, 1987 [DE] Germany ............... 37 30 859.9

[51] Int. Cl.⁶ .................. C09K 19/34; C09K 19/52; G02F 1/13
[52] U.S. Cl. ................ 252/299.61; 252/299.01; 359/103
[58] Field of Search ............. 252/299.01, 299.61; 359/103

[56] References Cited

U.S. PATENT DOCUMENTS

| | | | |
|---|---|---|---|
| 4,952,699 | 8/1990 | Yong et al. | 252/299.61 |
| 5,075,030 | 12/1991 | Togano et al. | 252/299.61 |
| 5,076,961 | 12/1991 | Nakamura et al. | 252/299.61 |
| 5,116,530 | 5/1992 | Togano et al. | 252/299.61 |
| 5,143,642 | 9/1992 | Krause et al. | 252/299.61 |
| 5,200,109 | 4/1993 | Iwaki et al. | 252/299.61 |
| 5,213,709 | 5/1993 | Takiguchi et al. | 252/299.61 |
| 5,366,657 | 11/1994 | Illian et al. | 252/299.61 |

FOREIGN PATENT DOCUMENTS

| | | | |
|---|---|---|---|
| 0206228 | 12/1986 | European Pat. Off. . | |
| 0239403 | 9/1987 | European Pat. Off. . | |
| 0244939 | 11/1987 | European Pat. Off. . | |
| 117014 | 12/1985 | German Dem. Rep. | 252/299.61 |
| 240385 | 10/1986 | German Dem. Rep. . | |
| 2403385 | 10/1986 | German Dem. Rep. | 252/299.61 |
| 240386 | 10/1986 | German Dem. Rep. | 252/299.61 |
| 247221 | 7/1987 | German Dem. Rep. | 252/299.61 |
| 247694 | 7/1987 | German Dem. Rep. | 252/299.61 |
| 285104 | 12/1990 | German Dem. Rep. . | |
| 285105 | 12/1990 | German Dem. Rep. . | |
| 3515373 | 11/1986 | Germany | 252/299.61 |
| 3627964 | 3/1987 | Germany . | |
| 3703651 | 9/1987 | Germany . | |
| 3801799 | 9/1988 | Germany | 252/299.61 |
| 3819972 | 1/1989 | Germany | 252/299.61 |
| 86/06401 | 11/1986 | WIPO . | |
| 86/07085 | 12/1986 | WIPO . | |

OTHER PUBLICATIONS

Dimitrowa, K., et al., J. Prakt. Chemie, vol. 322, No. 6, pp. 933–944 (1980).
Demus, D., et al., Flussige Kaistalle in Tabellem II, Veb Deutscher Verlag fur Grunbstoffinbustrie, Leipzig, pp. 356–361 (1984).
Gray, G. W., et al., Liquid Crystals & Plastic Crystals, vol. 1, Ellis Horwood Ltd., Chichester, UK., pp. 142–143 (1974).
Beresnev et al., Ferroelectrics, 59:1–10 (1984).
Dijon, Liquid Crystals—Applications and Uses, vol. 1, edited by Briendra Bahadur, Singapore, 1990, pp. 328–334.
Flüssige Kristalle in Tabellen II, pp. 4–27, 358–361, 456 and 457 (1984).
Pelzl et al., Mol. Cryst. Liq. Cryst., 1(1–2):39–44 (1985).
Dölling et al., J.f. Prakt. Chem., 321:643–654 (1979).
Dimitrowa et al., J.f. Prakt. Chem., 322:933–944 (1980).
Sackmann et al., Mol. Cryst. Liq. Cryst., 2:239–273 (1973).
Kristallin–flüssige Heterocyclen. Wiss. Z. Univ. Halle XIX'70 M, H.5, pp. 1–18.
Van Hecke et al., Liquid Crystals, 12(3):503–513 (1992).
Demus et al., Mol. Cryst. Liq. Cryst., 25:215–232 (1974).
Beresnev et al., Mol. Cryst. Liq. Cryst., 89:329–338 (1982).
English translation of Abstract of DD 240 385, Derwent (1987).

*Primary Examiner*—Shean Wu
*Attorney, Agent, or Firm*—Millen, White, Zelano, & Branigan

[57] ABSTRACT

The invention relates to the use of chiral and/or achiral compounds, containing at least one structural element from the group comprising thiazole-2,4-diyl thiazole-2,5-diyl 1,2,4-thiadiazole-2,5-diyl 1,2,4-thiadiazole-3,5-diyl as components of media having a smectic liquid-crystalline phase.

28 Claims, No Drawings

MEDIA CONTAINING THIAZOLE DERIVATIVES AND THIADIAZOLE DERIVATIVES AND HAVING A SMECTIC LIQUID-CRYSTALLINE PHASE

This application is a continuation of application Ser. No. 07/299,917, filed as PCT/EP88/00279, Apr. 5, 1988, now abandoned.

BACKGROUND OF THE INVENTION

The invention relates to the use of chiral and/or achiral compounds with a thiazole or thiadiazole structural element as components in media having a smectic liquid-crystalline phase. The invention also relates to media having a smectic liquid-crystalline phase, in particular having a chiral tilted smectic liquid-crystalline phase, which media contain compounds having a thiazole or thiadiazole structural element.

Media having chiral tilted smectic liquid-crystalline phases and ferro-electric properties can be prepared by adding a suitable chiral doping agent to base mixtures having one or more tilted smectic phases (L. A. Beresnev et al., Mol. Cryst. Liq. Cryst. 89, 327 (1982); H. R. Brand et al., J. Physique 44 (lett.), L-771 (1983)). Such media can be used as dielectrics for rapidly switching displays, which are based on the principle, described by Clark and Lagerwall, of SSFLC technology (N. A. Clark and S. T. Lagerwall, Appl. Phys. Lett. 36, 899 (t980); U.S. Pat. No. 4,367,924) as a result of the ferro-electric properties of the chiral tilted phase.

In this phase, the elongate molecules are arranged in layers, the molecules having a tilt angle relative to the perpendicular of the layer. When passing from layer to layer, the direction of tilt changes by a small angle relative to an axis perpendicular to the layers, so that a helix structure is formed. In displays based on the principle of SSFLC technology the smectic layers are arranged perpendicular to the plates of the cell. The helix-like arrangement of the tilt direction of the molecules is suppressed by a very small spacing of the plates (about 1–2 μm). As a result, the longitudinal axes of the molecules are forced to arrange in a plane parallel to the plates of the cell causing two preferential tilt orientations. Switching between these two states in the liquid-crystalline phase showing spontaneous polarization is possible by applying a suitable electric alternating field. This switching process is substantially faster than in conventional twisted cells (TN-LCD's) based on nematic liquid crystals.

In many applications, a great disadvantage of the currently available materials having chiral tilted smectic phases (such as, for example, Sc*, but also $S_H^*$, $S_I^*$, $S_J^*$, $S_K^*$, $S_G^*$, $S_F^*$) is their low chemical, thermal and light stability. A further disadvantageous property of displays based on currently available chiral tilted smectic mixtures is that the spontaneous polarization has unduly small values and/or the viscosity is unduly high, so that the switching time behavior of the displays is unfavorably affected and/or the pitch and tilt of the phases do not meet the requirements of display technology. Furthermore, the temperature range of the ferro-electric phases is in most cases too small and predominantly is at unduly high temperatures.

SUMMARY OF THE INVENTION

It has now been found that the use of chiral and/or achiral compounds, containing at least one structural element from the group comprising thiazole-2,4-diyl thiazole-2,5-diyl 1,3,4-thiadiazole-2,5-diyl 1,2,4-thiadiazole-3,5-diyl as components of chirally tilted smectic mixtures can substantially diminish the said disadvantages. These compounds are therefore outstandingly suitable as components of media having a chirally tilted smectic liquid-crystalline phase. In particular, it is possible with their aid to prepare chemically particularly stable media which have a chirally tilted smectic liquid-crystalline phase and favorable ferro-electric phase regions, in particular broad Sc*, phase regions, outstanding ability to be supercooled to temperatures below 0° C. without crystallization occurring, and spontaneous polarization values (in $nC/cm^2$) which are high for phases of this type.

Compounds with a thiadiazole structural element are admittedly known for use in liquid crystal materials, but only as nematic Liquid crystals (East German Patent 117, 014) or as non-liquid-crystalline additives in nematic liquid crystal mixtures (Japanese Application 50-92,279). However, there are no indications whatsoever to the effect that these compounds can be used as components of chiral tilted smectic mixtures for ferro-electric displays based, for example, on the SSFLC technology described by Clark and Lagerwall.

In German OffenLegungsschrift 3,627,964, chiral branched α-chlorocarboxylic acid derivatives are described as ferro-electric liquid crystals. The general formula which is given there and is worded very broadly can also comprise compounds which contain the 1,3,4-thiadiazole-2,5-diyl structural element. However, no such compound is concretely disclosed, so that it must be assumed that the particular value of neither this special class of compounds nor generally of compounds having a thiazole or thiadiazole structural element has been recognized or even exploited.

The invention thus relates to the use of chiral and/or achiral compounds, containing at Least one structural element from the group comprising thiazole-2,4-diyl thiazole-2,5-diyl 1,3,4-thiadiazole-2,5-diyl 1,2,4-thiadiazole-3,5-diyl as components of media having a smectic liquid-crystalline phase, in particular a chirally tilted smectic liquid-crystalline phase.

The invention also relates to media which have a smectic liquid-crystalline phase and contain such compounds, and to electro-optical display elements with such media as the dielectric.

Compounds having a thiazole or thiadiazole structural element are above all to be understood as those which can be represented by the general formula I

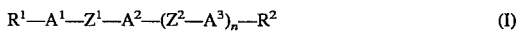

$$R^1—A^1—Z^1—A^2—(Z^2—A^3)_n—R^2 \qquad (I)$$

wherein at least one of the rings $A^1$, $A^2$ and $A^3$ is one of the groups thiazole-2,4-diyl, thiazole-2,5-diyl, 1,3,4-thiadiazole-2,5-diyl or 1,2,4-thiadiazole-3,5-diyl, $A^1$, $A^2$ and $A^3$ otherwise are each independently of one another a 1,4-phenylene group which is unsubstituted or mono- or poly-substituted by halogen, nitrile and/or alkyl and in which one or more CH groups can also be replaced by N, a 1,4-cyclohexylene group which is unsubstituted or CN-substituted and in which one or two non-adjacent $CH_2$ groups can also be replaced by O and/or S, or one of the groups 1,4-bicyclo(2,2,2)octylene, piperidine-1,4-diyl, naphthalene-2,6-diyl, decahydronaphthalene-2,6-diyl or 1,2,3,4-tetrahydronaphthalene-2,6-diyl, $R^1$ and $R^2$ are each independently of one another an alkyl group having 1–15 C atoms or an organic radical which is derived therefrom and can contain one or more of the groups —O—, —S—, —CO—, —O—CO—, —CO—O—, —CO—S—, —S—CO—, —CH(halogen)—, —CF$_2$—, —CHCN—, —C(alkyl)CN— and/or —CH=CH—, —C≡C— and, if appropriate, may have an asymmetric carbon atom causing optical activity, and one of the radicals $R^1$ and $R^2$ can also be F, Cl, Br, CN, COOH, OH, SH, NH$_2$, NO$_2$ or —NCS, $Z^1$ and $Z^2$ are each independently of one another —CO—O—, —O—CO—, —CH$_2$CH$_2$—, —CH$_2$—O—, —OCH$_2$—, —N=N—, —NO=N—, —CH=N— or a single bond, and one of the groups $Z^1$ and $Z^2$ can also be —CH$_2$—, —O—, —CO—, —CHCN—, —CH(halogen)—, —CH$_2$CH$_2$CH$_2$—, —CH$_2$—COO— or —CH$_2$OCO—, and n is 0, 1, 2 or 3.

To large extent, formula I also comprises novel compounds. These are above all compounds of the formula I with the definitions given above and with the proviso that at least one of the radicals $R^1$ and $R^2$ is an alkyl group which has 4–15 C atoms and in which at least one CH$_2$ group is replaced by —C(alkyl)CN— and, if appropriate, one or more further CH$_2$ groups can be replaced by —O—, —S—, —CO—, —O—CO—, —CO—O—, —CO—S—, —S—CO—, —CH(halogen)—, —CF$_2$—, —CHCN—, —CH=CH—, and/or —C≡C—.

The invention also relates to the novel compounds of the formula I. These are in particular compounds of the formula I

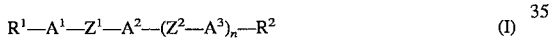

wherein at least one of the rings $A^1$, $A^2$ and $A^3$ is one of the groups thiazole-2,4-diyl, thiazole-2,5-diyl, 1,3,4-thiadiazole-2,5-diyl or 1,2,4-thiadiazole-3,5-diyl, $A^1$, $A^2$, $A^3$ otherwise are each independently of one another a 1,4-phenylene group which is unsubstituted or mono- or poly-substituted by halogen nitrile and/or alkyl and in which one or more CH groups can also be replaced by N, a 1,4-cyclohexylene group which is unsubstituted or CN-substituted and in which one or two non-adjacent CH$_2$ groups can also be replaced by O and/or S, or one of the group 1,4-bicyclo(2,2,2)octylene, piperidine-1,4-diyl, naphthalene-2,6-diyl, decahydronaphthalene-2,6-diyl or 1,2,3,4-tetrahydronaphthalene-2,6-diyl, $R^1$ and $R^2$ are each independently of one another an alkyl group having 1–15 C atoms or an organic radical which is derived therefrom and can contain one or more of the groups —O—, —S—, —CO—, —O—CO—, —CO—O—, —CO—S—, —S—CO—, —CH(halogen)—, —CF$_2$—, —CHCN—, —C(alkyl)CN— and/or —CH=CH=, —C≡C— and, if appropriate, may have an asymmetric carbon atom causing optical activity, no two heteroatoms being directly linked to one another, and one of the radicals $R^1$ and $R^2$ can also be F, Cl, Br, CN, COOH, OH, SH, NH$_2$, NO$_2$ or —NCS, $Z^1$ and $Z^2$ each independently of one another are —CO—O—, —O—CO—, CH$_2$CH$_2$—, —CH$_2$—O—, —OCH$_2$—, —N=N—, —NO=N—, —CH=N— or a single bond, and one of the groups $Z^1$ and $Z^2$ can also be —CH$_2$—, —O—, —CO—, —CHCN—, —CH(halogen)—, —CH$_2$CH$_2$CH$_2$—, —CH$_2$—COO— or —CH$_2$OCO—, and is 0, 1, 2 or 3, with the proviso that at least one of the radicals $R^1$ and $R^2$ is an alkyl group which has 4–15 C atoms and in which at least one CH$_2$ group is replaced by —C(alkyl)CN— and, if appropriate, one or more further CH$_2$ groups can be replaced by —O—, —S—, —CO—, —O—CO—, —CO—O—, —CO—S—, —S—CO—, —CH(halogen)—, —CF$_2$—, —CHCN—, —CH=CH— and/or —C≡C—.

Moreover, these include thiadiazole derivatives of the formula

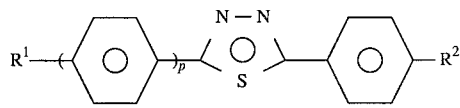

wherein p is 0 or 1, one of the groups $R^1$ and $R^2$ is

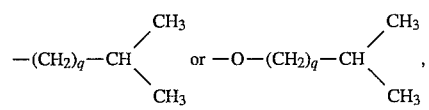

in which q can be 2 to 7, especially 3, and the other of the groups $R^1$ and $R^2$ is straight-chain alkyl or alkoxy having 3 to 12 C atoms, and thiadiazole derivatives of the formula

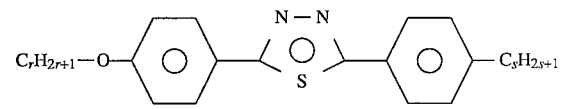

wherein r is 6, 8, 9 or 10 and s is 5, 6, 7, 8, 9, 10, 11 or 12 and the groups $C_rH_{2r+1}$ and $C_sH_{2s+1}$ are preferably straight-chain alkyl groups.

The compounds of the formula I have a wide range of applications. Depending on the choice of substituents, these compounds can be added to liquid-crystalline base materials from other classes of compounds for example in order to vary the dielectric and/or optical anisotropy and/or the viscosity and/or the spontaneous polarization and/or the pitch and/or the phase range of such a dielectric, but they can also be used as base materials of which liquid-crystalline media are predominantly composed.

The compounds of the formula I are also suitable as intermediates for the preparation of other substances which can be used as constituents of liquid-crystalline dielectrics.

In addition, the range of liquid-crystalline substances, which are suitable for the preparation of liquid-crystalline mixtures under various technological aspects, is quite generally widened considerably by the provision of the compounds of the formula I.

According to the indicated definitions for $R^1$, $R^2$, $A^1$, $A^2$, $A^3$, $Z^1$, $Z^2$ and n, formula I comprises compounds having 2 to 5 rings, at least one of which is a cyclic structural element from the group comprising thiazole-2,4-diyl, thiazole-2,5-diyl, 1,3,4-thiadiazole-2,5-diyl and 1,2,4-thiadiazole-3,5-diyl.

Preferably, only one of the rings $A^1$, $A^2$ and $A^3$ is one of the structural elements designated above; 1,3,4-thiadiazole-2,5-diyl is particularly preferred here.

Accordingly, the compounds of the formula I comprise compounds having two of the part formulae Ia and Ib:

$R^1$—$A^1$—$A^2$—$R^2$    Ia $R^1$—$A^1$—$Z^1$—$A^2$—$R^2$    Ib, compounds having three rings of the part formulae Ic to Ie:

$R^1$—$A^1$—$A^2$—$A^3$—$R^2$    Ic $R^1$—$A^1$—$Z^1$—$A^2$—$A^3$—$R^2$    Id $R^1$—$A^1$—$Z^1$—$A^2$—$Z^2$—$A^3$—$R^2$    Ie, compounds having four rings of the part formulae If to Ik:

$R^1$—$A^1$—$A^2$—$A^3$—$A^3$—$R^2$    If $R^1$—$A^1$—$Z^1$—$A^2$—$A^3$—$A^3$—$R^{2tm}$    Ig $R^1$—$A^1$—$A^2$—$Z^2$—$A^3$—$A^3$—$R^2$    Ih $R^1$—$A^1$—$Z^1$—$A^2$—$Z^2$—$A^3$—$A^3$—$R^2$    Ii $R^1$—$A^1$—$Z^1$—$A^2$—$A^3$—$Z^2$—$A^3$—$R^2$    Ij $R^1$—$A^1$—$Z^1$—$A^2$—$Z^2$—$A^3$—$Z^2$—$A^3$—$R^2$    Ik and compounds having five rings of the part formulae Il to It:

$R^1$—$A^1$—$A^2$—$A^3$—$A^3$—$A^3$—$R^2$    Il $R^1$—$A^1$—$Z^1$—$A^2$—$A^3$—$A^3$—$A^3$—$R^2$    Im $R^1$—$A^1$—$A^2$—$Z^2$—$A^3$—$A^3$—$A^3$—$R^2$    In $R^1$—$A^1$—$Z^1$—$A^2$—$Z^2$—$A^3$—$A^3$—$A^3$—$R^2$    Io $R^1$—$A^1$—$Z^1$—$A^2$—$A^3$—$Z^2$—$A^3$—$A^3$—$R^2$    Ip $R^1$—$A^1$—$Z^1$—$A^2$—$A^3$—$A^3$—$Z^2$—$A^3$—$R^2$    Iq $R^1$—$A^1$—$Z^1$—$A^2$—$Z^2$—$A^3$—$Z^2$—$A^3$—$A^3$—$R^2$    Ir $R^1$—$A^1$—$Z^1$—$A^2$—$Z^2$—$A^3$—$A^3$—$Z^2$—$A^3$—$R^2$    Is $R^1$—$A^1$—$Z^1$—$A^2$—$Z^2$—$A^3$—$Z^2$—$A^3$—$Z^2$—$A^3$—$R^2$    It

Those compounds are preferred which have 2 or 3 rings, especially those of the formulae Ia and Ic. Dinuclear compounds of the formula Ia are particularly preferred.

If $A^1$, $A^2$, and $A^3$ are not one of the thiazole or thiadiazole ring structural elements indicated above, these can each independently of one another be a 1,4-phenylene group which is unsubstituted or mono- or polysubstituted by halogen, nitrile and/or alkyl and in which one or more CH group can also be replaced by N, a 1,4-cyclohexylene group which is unsubstituted or CN-substituted and in which one or two non-adjacent $CH_2$ groups can also be replaced by O and/or S, or are the groups 1,4-bicyclo(2,2,2)octylene, piperidine-1,4-diyl, naphthalene-2,5-diyl, decahydronaphthalene-2,6-diyl or 1,2,3,4-tetrahydronaphthalene-2,6-diyl.

For the sake of simplicity, Cy below is a 1,4-cyclohexylene group, Dio is a 1,3-dioxane-2,5-diyl group, Dit is a 1,4-dithiane-2,5-diyl group, Bi is a bicyclo[2,2,2] octylene group, Pip is a piperidine-1,5-diyl group, Phe is a 1,4-phenylene group, Py is a pyridine-2,5-diyl group, Pyr is a pyrimidine-2,5-diyl group and Pyn is a pyridazine-3,6-diyl group, it being possible for Phe and/or Py and/or Pyr and/or Pyn to be unsubstituted or mono- or di-substituted by F and/or Cl atoms and/or $CH_3$ groups and/or CN groups.

$A^1$, $A^2$ and $A^3$ are preferably Cy, Phe, Py, Dio or Pyr; preferably, the compounds of the formula I each do not contain more than one of the radicals Dio, Dit, Pip, Bi, Pyn and Pry.

$R^1$ and $R^2$ can each independently of one another be an alkyl group having 1–15 C atoms or an organic radical which is derived therefrom and can contain one or more groups —O—, —S—, —CO—, —O—CO—, —CO—O—, —CO—S—, —S—CO—, —CH(halogen)—, —$CF_2$—, —CHCN—, —C(alkyl)CN— and/or —CH=CH— and, if appropriate, an asymmetric carbon atom causing optical activity, or one of the radicals $R^1$ and $R^2$ can also be F, Cl, Br, CN, COOH, OH, SH, $NH_2$, $NO_2$ or —NCS.

$R^1$ and $R^2$ are preferably alkyl or alkoxy and also polyfluoroalkyl, each having 1–15 C atoms.

Those compounds are also preferred in which one of the radicals $R^1$ and $R^2$ is CN, —NCS, F or Cl.

If $R^1$ and $R^2$ are alkyl radicals and/or alkoxy radicals, they can be straight-chain or branched. Preferably, they are straight-chain, have 1 to 15, especially 2 to 12, C atoms and, accordingly, are preferably ethyl, propyl, butyl, pentyl, hexyl, heptyl, octyl, nonyl, decyl, undecyl, dodecyl, ethoxy, propoxy, butoxy, pentoxy, hexoxy or heptoxy, octoxy, nonoxy, decyloxy, undecyloxy, dodecyloxy and also methyl, tridecyl, tetradecyl, pentadecyl, methoxy, tridecyloxy, tetradecyloxy or pentadecyloxy.

Those compounds of the formula I are particularly preferred which contain different wing groups $R^1$ and $R^2$ in the molecule, such as preferably alkyl and aLkoxy groups. Compounds which simultaneously contain alkyl and alkoxy wing groups lead to markedly lower melting points in ferro-electric liquid-crystalline mixtures.

The compounds of the formula I of the part formulae given above and below, having branched wing groups $R^1$ and/or $R^2$, may sometimes be important because of a higher solubility in the usual liquid-crystalline base materials, but especially as chiral doping substances for chiral tilted smectic phases, if they are optically active. For this purpose, it is necessary that the radicals $R^1$ and/or $R^2$ have at least one asymmetric carbon atom causing optical activity.

Formula I then comprises both the racemate of these compounds and the optical antipodes and mixtures thereof. However, such compounds are also suitable as components of nematic liquid-crystalline phases, in particular for avoiding reverse twist. Branched groups of this type contain, as a rule, one or two chain branchings. Preferably, the asymmetric carbon atom is linked to two C atoms with different substitution, one H atom and one substituent selected from the group comprising halogen (especially F, Cl or Br), alkyl or alkoxy each having 1 to 5 C atoms, and CN. The optically active organic radical $R^1$ and/or $R^2$ is preferably of the formula

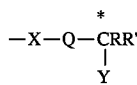

wherein

X is —CO—O—, —O—CO—, —O—CO—O—, —CO—, —S—, —CH=CH—, —CH=CH—COO— or a single bond, Q is alkylene having 1 to 5 C atoms, wherein a $CH_2$ group not linked to X can also be replaced by —O—, —CO—, —O—CO—, —CO—O— or —CH=CH—, or a single bond, Y is CN, halogen, methyl or methoxy and R and R' are different from one another and from Y and are each H or an alkyl or alkoxy group which has 1 to 18 C atoms and in which one or two non-adjacent $CH_2$ groups can also be replaced by —O—, —CO—, —O—CO—, —CO—O— and/or —CH=CH—.

X is preferably —CO—O—, —O—CO—, —CH=CH—COO— (trans) or a single bond. —CO—O— and —O—O and especially —CO—O— are particularly preferred.

Q is preferably —CH$_2$—, —CH$_2$CH$_2$— or a single bond, a single bond being particularly preferred.

Y is preferably CH$_3$, —CN or F, —CN or F being particularly preferred.

R and R' are preferably branched or straight-chain alkyl having 1 to 10 and especially 1 to 7 C atoms.

Preferred branched radicals R$^1$ and R$^2$ are isopropyl, 2-butyl(=1-methylpropyl), isobutyl(=2-methylpropyl), 2-methylbutyl, isopentyl(=3-methylbutyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl, 2-octyloxy, 2-chloropropionyloxy, 2-fluoro-3-methylbutyryloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl and 2-cyano-2-methylhexanoyloxy.

Compounds of the formula I, wherein one of the radicals R$^1$ and R$^2$ is of the formula —X—Q—CHCN—R (with the preferred meanings given above), can be prepared, for example, according to D. A. Evans and J. M. Takacs, Tetrahedron Lett. 21, 4233 (1980).

Polyfluoroalkyl groups, wherein one or more CF$_2$ groups can also be replaced by a grouping selected from the group comprising —O—, —S—, —CO—, —CH(halogen)—, —CHCN—, —O—CO—, —O—COO—, —CO—O— and —CH=CH— or also by a combination of two suitable groupings, no two hetero atoms being directly linked to one another, are preferably perfluoroalkyl groups having 1 to 15 C atoms, wherein 1 to 3 CH$_2$ groups can also be replaced by a grouping selected from the group comprising —O—, —CH(halogen)— (especially —CHF—), —O—CO—, —CO—O— and —O—COO— or also by a combination of two suitable groupings, no two hetero atoms being directly linked to one another.

Particularly preferred groups are those of the formulae R$_F$, R$_F$CH$_2$, R$_F$CH$_2$CH$_2$, R$_F$CH$_2$O and R$_F$COO.

R$_F$ is preferably a straight-chain perfluoroalkyl group having preferably 2 to 12 C atoms, wherein one or more fluorine atoms (preferably 1 or 2 fluorine atoms, preferably in the ω-position or (ω-1)-position) can also be replaced by H.

Preferred compounds of the formula I, wherein at least one of the radicals R$^1$ and R$^2$ is a polyfluoroalkyl group, lead to phases according to the invention which have a low optical anisotropy and a pronounced S$_A$ phase at elevated temperatures.

Z$^1$ and Z$^2$ can each independently of one another be —CO—O—, —O—CO—, —CH$_2$CH$_2$—, —CH$_2$—O—, —OCH$_2$—, —N=N—, —NO=N—, —CH=N— or a single bond; one of the groups Z$^1$ and Z$^2$ can also be —CH$_2$—, —O—, —CO—, —CHCN—, —CH(halogen)—, —CH$_2$CH$_2$CH$_2$—, —CH$_2$—COO— or —CH$_2$OCO—.

Z$^1$ and Z$^2$ are preferably single bonds and, by second preference, —CO—O—, —O—O— or —CH$_2$CH$_2$— groups.

The following smaller groups of compounds in which —A— is thiazole-2,4-diyl, thiazole-2,5-diyl, 1,3,4-thiadiazole-2,5-diyl and 1,2,4-thiadiazole-3,5-diyl, are particularly preferred. Alkyl is here methyl, ethyl, propyl, butyl and preferably straight-chain pentyl, hexyl, heptyl, octyl, nonyl or decyl; alkoxy and oxyalkoxy are methoxy, ethoxy, propoxy, butoxy and preferably straight-chain pentoxy, hexoxy, heptoxy, octoxy, nonoxy or decyloxy:

alkyl-Phe-A-alkyl
alkoxy-Phe-A-alkyl
alkyl-OCO-Phe-A-alkyl
alkyl-Cyc-A-alkyl
alkoxy-Cyc-A-alkyl
alkyl-COO-Cyc-A-alkyl
alkyl-OCO-Cyc-A-alkyl
alkyl-Phe-Phe-A-alkyl
alkoxy-Phe-Phe-A-alkyl
alkyl-Phe-A-Phe-alkyl
alkoxy-Phe-A-Phe-alkyl
alkoxy-Phe-A-Phe-alkoxy
alkyl-Phe-Cyc-A-alkyl
alkyl-Phe-Phe-Cyc-A-alkyl
alkoxy-Phe-Cyc-A-alkyl
alkoxy-Phe-Phe-Cyc-A-alkyl
alkyl-Phe-CH$_2$-CH$_2$-A-alkyl
alkyl-Phe-Phe-CH$_2$CH$_2$-A-alkyl
alkoxy-Phe-CH$_2$CH$_2$-A-alkyl
alkoxy-Phe-Phe-CH$_2$CH$_2$-A-alkyl
alkyl-Cyc-Cyc-A-alkyl
alkyl-CyC-A-Phe-alkyl
alkoxy-Cyc-A-Phe-alkyl
alkoxy-Phe-A-Cyc-alkyl
alkyl-Py-A-alkyl
alkyl-Pyr-A-alkyl
alkyl-Cyc-COO-Phe-A-alkyl The compounds of the formula I are prepared by methods known per se and under the reaction conditions conventional for this purpose, such as are described in the literature (for example in the standard text books such as Houben-Weyl, Methoden der Organischen Chemie [Methods of Organic Chemistry], Georg-Thieme-Verlag, Stuttgart), especially in the publication known to a person skilled in the relevant art of the chemistry of liquid-crystalline compounds.

The introduction of the thiazole or thiadiazole structural elements can, on the one hand, be effected by converting precursors, which already contain these structural elements, by the known methods into the compounds of the formula I. On the other hand, however, heterocyclic thiazole or thiadiazole radicals can also be produced in appropriately structured precursors or substructural units of the compounds of the formula I by methods known per se.

Thus, for example, 2,5-disubstituted 1,3,4-thiadiazoles can be prepared by reacting N,N'-diacylhydrazines with usual thiation reagents such as P$_4$S$_{10}$ or Lawesson's reagent.

The media according to the invention having a smectic liquid-crystalline phase consist of 2 to 25, preferably 3 to 15, components including at least one compound of the formula I.

The most important compounds which can be used as constituents of such liquid-crystalline media can be characterized by the formula II,

R$^3$—L—G—E—R$^4$   (II)

wherein L and E each are a carbocyclic or heterocyclic ring system from the group comprising 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is a structural element from the group comprising

| | |
|---|---|
| —CH=CH— | —N(O)=N— |
| —CH=CY— | —CH=N(O)— |
| —C≡C— | —CH$_2$—CH$_2$— |
| —CO—O— | —CH$_2$—O— |
| —CO—S— | —CH$_2$—S— |
| —CH=N— | —COO—Phe—COO— | or a C—C single bond with Y=halogen, preferably chlorine, or —CN, and R$^3$ and R$^4$ are alkyl, alkoxy, alkanoyloxy or alkoxycarbonyloxy having up to 18 and preferably up to 8 carbon atoms, or one of these radicals can also be CN, NCS, NO$_2$, CF$_3$, F, CL or Br.

In most of these compounds, R$^3$ and R$^4$ differ from one another, one of these radicals being an alkyl or alkoxy group in most cases. However, other variants of the envisaged substituents are also usual. Many such substances or even mixtures thereof are commercially available. All these substances can be prepared by methods known from the literature.

The media according to the invention having a smectic liquid-crystalline phase contain about 0.1 to 99%, preferably 10 to 95%, of one or more compounds of the formula I. Liquid-crystalline media which contain 0.1–50%, especially 0.5–30%, of one or more compounds of the formula I are also preferred. Isotropic compounds of the formula I can also be used in the media according to the invention.

Those media according to the invention having a chiral tilted smectic liquid-crystalline phase are particularly preferred whose achiral base mixture contains, in addition to compounds of the formula I, at least one other component with a small amount of dielectric anisotropy, low viscosity and a wide S$_c$ phase region. This or these further component(s) of the achiral base mixture can, for example, amount to 40 to 90%, preferably 50 to 80%, of the base mixture. Suitable components are especially compounds of the part formuale IIa and IIb

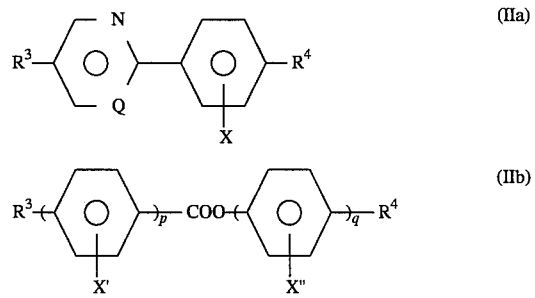

wherein R$^3$ and R$^4$ each independently of one another are alkyl or alkoxy having 5 to 12 C atoms, Q is CH or N, X, X' and X" each independently of one another are H or F and p and q are each 1 or 2, with the proviso that (p+q) is 2 or 3.

Components of the part formula IIc to IIk are particularly preferred:

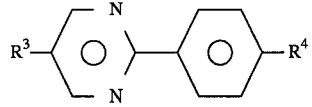

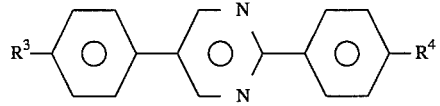

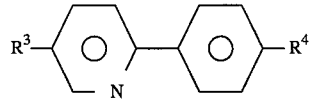

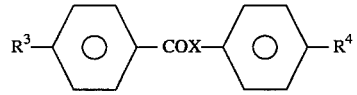

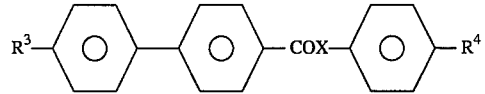

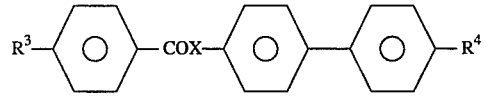

R$^3$ and R$^4$ each are preferably alkyl, alkoxy, alkanoyloxy or alkoxycarbonyl each having 3 to 12 C atoms. X is O or NH, preferably O. In the compounds of the formula IIc to IIk, a 1,4-phenylene group can also be laterally substituted by halogen, particularly preferably by fluorine. Preferably, one of the groups R$^3$ and R$^4$ is alkyl and the other group is alkoxy.

Those compounds of the part formulae IIc to IIk are particularly preferred in which R$^3$ and R$^4$ each are straight-chain alkyl or alkoxy each having 5 to 10 C atoms.

Ferro-electric liquid crystal mixtures which contain thiazole derivatives and/or thiadiazole derivatives and have particularly advantageous properties such as an especially low viscosity and an especially short switching time, contain a high proportion, preferably 70–80%, of dinuclear substances having a smectic phase C and a smaller proportion, preferably 10–25%, of trinuclear substances which are distinguished by a very high transition between the smectic phases C and A, and between the smectic phase C and the nematic or isotropic phase. Furthermore, such mixtures contain a chiral doping substance, preferably in a proportion of 5–15%.

Such mixtures show a wide region of the smectic base C with a transition to the smectic phase A at more than 60° C., a smectic phase A which is up to 200° C. wide, a negative dielectric anisotropy, a favorable tilt angle and very low viscosities. They allow very rapid switching times (for example 30 µs at room temperature).

The media according to the invention having a smectic Liquid-crystalline phase are prepared in a manner conventional per se. As a rule, the components are dissolved in one another, advantageously at an elevated temperature.

EXAMPLES

The examples which follow are intended to explain the invention without restricting it. Percentage data <above and below are percent by weight; all temperatures are given in degrees C. The other symbols mean: K: crystalline-solid state, S: smectic phase (the index indicates the phase type), N: nematic state, Ch: cholesteric phase, I: isotropic phase. The number given between two symbols indicates the transformation temperature in degrees C.

Example 1

31.3 g of 4-hydroxybenzoic acid hydrazide are suspended in 600 ml of pyridine and 208 ml of octanoic acid chloride are added dropwise at 15°–20° C., and the mixture is heated to 100° stirred for a further 1½ hours. After cooling, the reaction mixture is poured into 3 l of ice/water and the precipitate is filtered off with suction, rinsed with water and recrystallized from 2.2 l of methanol. This gives 178 g of N-(4-octanoylxybenzoyl)-N'-octanoylhydrazine of melting point 131° C.

40.5 g of this compound are dissolved in 500 ml of THF with heating, the solution is cooled to room temperature, 44.5 g of Lawesson's reagent are added and the mixture is stirred for a further 23 hours. About ⅔ of the THF are then distilled off, the residue is stirred into 1 l of water and 100 ml of 32% sodium hydroxide solution, and the precipitated crystals are filtered off with suction, washed with water until neutral, dried and recrystallized from ethanol. This gives 36.4 g of 2-(4-n-octanoyloxyphenyl)-5-n-heptyl-1,3,4-thiadiazole. K 78 S (77.5) I.

Example 2

30 g of the compound described above, 9 g of sodium hydroxide, 104 ml of water and 200 ml of ethanol are heated for 2 hours under reflux. The ethanol is largely distilled off and the residue is diluted with 500 ml of water, acidified and then rendered alkaline with sodium bicarbonate. This gives 17.5 g of 2-(4-hydroxyphenyl)-5-n-heptyl-1,3,4-thiadiazole of melting point 100° C..

8.5 g of the hydroxy compound are suspended with 2.5 ml of pyridine in 50 ml of toluene, and 6.7 g of trans-4-n-pentylcyclohexanecarboxylic acid chloride are added dropwise at room temperature. The mixture is stirred for a further 2 hours at 80°, the pyridine hydrochloride is filtered off with suction, the toluene phase is washed with water until neutral and, after stripping off the solvent, the product is recrystallized from ethanol. This gives 10.5 g of 2-[4-(trans-4-n-pentylcyclohexanoyloxy)-phenyl-5-n-heptyl-1,3,4,-thiadiazol. K 101 S 171 N 175 I.

Example 3

46.8 g of 4-n-decyloxybenzoic acid hydrazide are dissolved in 320 ml of pyridine. 23.7 ml of heptafluorobutyric acid chloride are added dropwise at room temperature and the mixture is stirred for a further 1½ hours. It is then poured on 1600 ml of ice/water, and the crystals are filtered off with suction and rinsed with water. Recrystallization from toluene gives 39.9 g of N-(4-n-decyloxybenzoyl)-N'-heptafluorobutyrylhydrazine of melting point 88° C.

37.5 g of this compound and 34.3 g of Lawesson's reagent are heated in 385 ml of THF for 10 hours under reflux. About ⅔ of the solvent are distilled off, the residue is poured into 800 ml of water and 80 ml of 32% strength sodium hydroxide solution, the mixture is filtered with suction and the precipitate is crystallized from ethanol with addition of active charcoal.

This gives 30 g of 2-(4-n-decyloxyphenyl)-5-heptafluoropropyl-1,3,4-thiadiazole. K 79 I.

Example 4

8.64 g of (S)-N-(4-n-decyloxybenzoyl)-N'-2-methyloctanoyl-hydrazine and 8.9 g of Lawesson's reagent are heated in 100 ml of THF for 5 hours under reflux. After working up as in the preceding example, this gives 7.3 g of (S)-2-(4-n-decyloxyphenyl)-5-(1-methylheptyl)-1,3,4-thiadiazole.

Example 5

13.6 g of (S)-2-chloroisovaleric acid, 1.35 g of 4-dimethylaminopyridine and 30.6 g of 2-(4-hydroxyphenyl)-5-n-nonyl-1,3,4-thiadiazole are introduced into 150 ml of dichloromethane, a solution of 21.9 g of dicyclohexylcarbodiimide in 30 ml of dichloromethane is added dropwise at 10° with stirring and the mixture is then stirred for a further 15 hours at room temperature. The product is filtered off with suction over silica gel, the solvent evaporated and the residue is recrystallized from ethanol, giving 28.3 g of (S)-2-4-(2-chloroisovaleroyloxy)phenyl-5-n-nonyl-1,3,4-thiadiazole.

Example 6

7.5 g of N-(4-heptyloxybenzoyl)-N'-octanoyl-hydrazine are dissolved in 100 ml of THF with heating, the cooled to 20° C. and 8.9 g of Lawesson's reagent are added. After stirring for seventeen hours, the product is poured onto a mixture of 300 ml of ice/water and 28 ml of 32% strength sodium hydroxide solution. The precipitated crystals are filtered off with suction, rinsed with water and recrystallized from 56 ml of ethanol. This gives 6.5 g of 2-(4-n-heptanoyloxyphenyl)-5-n-heptyl-1,3,4-thiadiazole.

Examples 7–64

The following are prepared analogously:

2(4-n-Octanoyloxyphenyl)-5-n-heptyl-1,3,4-thiadiazole K 78 $S_C$ 79 I.

2-(4-n-Heptyloxyphenyl)-5-n-heptyl-1,3,4-thiadiazole K 79 $S_C$ 89 I.

2-(4-n-Heptyloxyphenyl)-5-n-nonyl-1,3,4-thiadiazole K 77 $S_C$ 89 I.

2-(4-n-Octyloxyphenyl)-5-n-pentyl-1,3,4-thiadiazole K 67 K 73 $S_C$ (69) $S_A$ 81 I.

2-(4-n-Octyloxyphenyl)-5-n-hexyl-1,3,4-thiadiazole K 73 $S_C$ 80 $S_A$ 83 I.

2-(4-n-Octyloxyphenyl)-5-n-heptyl-1,3,4-thiadiazole K80 $S_C$ 87 I.

2-(4-n-Decyloxyphenyl)-5-n-heptyl-1,3,4-thiadiazole K 70 $S_C$ 89 I.

2-(4-n-Octyloxyphenyl)-5-(4'-n-heptylphenyl)-1,3,4-thiadiazole K 78 $S_C$ 171 N 178 I.

2,5-Bis(4-n-pentylphenyl)-1,3,4-thiadiazole K 93 $S_C$ 123 N 164 I.

2,5 -Bis(4-n-heptylphenyl)-1,3,4-thiadiazole K 81 $S_C$ 149 N 158 I.

2,5 -Bis(4-n-octyloxyphenyl)-1,3,4-thiadiazole K 101 $S_C$ 194 N 196 I.

2,5 -Bis(4-n-nonyloxyphenyl)-1,3,4-thiadiazole K 93 $S_C$ 187 I.

2-(4-n-Nonyloxyphenyl)-5-[4'-(2-methylbutyl)phenyl]-1,3,4-thiadiazole K 112 $S_C$ 133 N*, 150 I.

1-(4-n-Nonyloxyphenyl)-5-[4'-(2-methylbutyloxy)phenyl]-1,3,4-thiadiazole K 90 $S_C$ 157 N*, 163.5 I.
2-(4-n-Nonyloxyphenyl)-5-[4'-(2-methylbutyloxy)phenyl]-1,3,4-thiadiazole K 90 $S_C$ 169 N 182 I.
2-(4-n-Nonyloxyphenyl)-5-(4'-butyloxyphenyl)-1,3,4-thiadiazole K 97 $S_C$ 179 N 201 I.
2-(2-Fluoro-4-n-octyloxyphenyl)-5-(4'-n-nonyloxyphenyl)-1,3,4-thiadiazole K 94 $S_C$ 130 $S_A$ 165 N 178.7 I.
2-(2-Fluoro-4-n-octyloxyphenyl)-5-[4'-(2-methylbutyl)phenyl]-1,3,4-thiadiazole K 112 $S_C$ 141 I.
2-n-Butyl-5-(4'-n-octyloxybiphenyl-4-yl)-1,3,4-thiadiazole K 126 $S_C$ 149 $S_A$ 209 I.
2-n-Pentyl-5-(4'-n-octyloxybiphenyl-4-yl)-1,3,4-thiadiazole K 134 $S_G$ 146 $S_I$ 158 $S_C$ 194 $S_A$ 212 I.
2-n-Nonyl-5-[4'-(3-methylbutyloxy)-biphenyl-4-yl]-1,3,4-thiadiazole K 75 $S_C$ 126 I.
2-n-Nonyl-5-(2-fluoro-4'-n-propylbiphenyl-4-yl)-1,3,4-thiadiazole K 84 $S_C$ 93 N 123 I.
2-(4-n-Decylphenyl)-4-(4'-methoxyphenyl)-thiazole K 95 N 154 I.
2-(4-n-Decylphenyl)-4-(4'-n-hexyloxyphenyl)-thiazole K 43 $S_C$ 53 $S_A$ 142 I.
2-(4-n-Decylphenyl)-4-(4'-n-heptyloxyphenyl)-thiazole K 54 $S_B$ 64 $S_C$ 110 $S_A$ 143 I.
2-(4-n-Decylphenyl)-4-(4'-n-octyloxyphenyl)-thiazole K 59 $S_B$ 73 $S_C$ 120 $S_A$ 146 I.
2-(4-n-Decylphenyl)-4-(4'-n-decyloxyphenyl)-thiazole K 66 $S_B$ 84 $S_C$ 137 $S_A$ 144.6 I.
2-(4-n-Octyloxyphenyl)-5-(4'-n-pentylphenyl)-1,3,4-thiadiazole K 80 $S_C$ 167 N 181.5 I.
2-(4-n-Octyloxyphenyl)-5-(4'-n-decylphenyl)-1,3,4-thiadiazole K 79 $S_C$ 173 I.
p-(5-n-Heptyl-1,3,4-thiadiazol-2-yl)-phenyl r-1-cyano-1-n-heptylcyclohexane-cis-4-carboxylate K 73 $S_F$ (66) $S_C$ 77 $S_A$ 167 I.
2-(4-n-Octyloxyphenyl)-5-n-octyl-1,3,4-thiadiazole K 80 $S_C$ 90 I.
2-(4-n-Octyloxyphenyl)-5-n-nonyl-1,3,4-thiadiazole K 77 $S_C$ 90 I.
2-(4-A-Decyloxyphenyl)-5-n-pentyl-1,3,4-thiadiazole K 73 $S_F$ (55) $S_C$ (57) $S_A$ 84 I.
2-(4-n-Decyloxyphenyl)-5-n-nonyl-1,3,4-thiadiazole K 79 $S_C$ 92 I.
2-(4-n-Hexyloxyphenyl)-5-(4'-n-pentylphenyl)-1,3,4-thiadiazole K 55 $S_C$ 158 N 186 I.
2-(4-n-Octylphenyl)-5-(3'-n-pentylcyclopentyl)-1,3,4-thiadiazole K 63 I.
2-[4-(3,7-Dimethyloctyloxy)-phenyl]-5-n-heptyl-1,3,4-thiadiazole K 48 I.
2-(4-n-Decyloxyphenyl)-5-(4'-n-heptylcyclohexyl)-1,3,4-thiadiazole K 97 $S_C$ 146.6 $S_A$ 170 I.
2-(4-n-Hexyloxyphenyl)-5-(4'-n-propylcyclohexyl)-1,3,4-thiadiazole K 59 $S_C$ (56) $S_A$ 119 N 143.9 I.
2-[4-(2-n-Heptyloxypropionyloxy)-phenyl]-5-(4'-n-octyloxyphenyl)-1,3,4-thiadiazole K 87 $S_C$* 141 I.
2-[4-(2-Methylbutyroyloxy)-phenyl]-5-(4'-n-octyloxyphenyl)-1,3,4-thiadiazole K 93 $S_C$ 163 I.
2-[4-(2-Chloro-3-methylbutyroyloxyphenyl)-5-(4'-n-octyloxyphenyl)-1,3,4-thiadiazole K 112 $S_C$* 166 Ch 170.7 I.
2-(4-n-Decyloxyphenyl )-5-[4'-(4-methylpentyl)-phenyl]-1,3,4-thiadiazole K 79 K87 $S_C$ 157 N 160.2 I.
2-(4-n-Hexylphenyl)-5-(4'-n-decylphenyl)-1,3,4-thiadiazole K 66 $S_C$ 168 N 172.9 I.
2-(4-n-Octyloxyphenyl)-5-(4'-perfluorohexylphenyl)-1,3,4-thiadiazole K 178 $S_C$ 187 $S_A$ 217 I.
2-(4-n-Octyloxyphenyl)-5-n-decyl-1,3,4-thiadiazole K 78 $S_G$ (70) $S_C$ 90 I.
2-(4-n-Nonyloxyphenyl)-5-n-hexyl-1,3,4-thiadiazole K 62 $S_G$ (61) $S_C$ 81 $S_A$ 83 I.
2-(4-n-Nonyloxyphenyl)-5-n-nonyl-1,3,4-thiadiazole K 76 $S_C$ 90 I.
2-(4-n-Decyloxyphenyl)-5-n-hexyl-1,3,4-thiadiazole K 62 $S_C$ 80 $S_A$ 84 I.
2-(4-n-Heptyloxyphenyl)-5-n-decyl-1,3,4-thiadiazole K 75 $S_C$ 86 I.
2-(4-n-Nonyloxyphenyl)-5-n-pentyl-1,3,4-thiadiazole K 69 $S_G$ (53) $S_C$ (66) $S_A$ 82 I.
2-(4-n-Heptyloxyphenyl)-5-n-pentyl-1,3,4-thiadiazole K 72 $S_C$ 74 $S_A$ 79 I.
2-(4-n-Heptyloxyphenyl)-5-n-hexyl-1,3,4-thiadiazole K 74 $S_C$ 81 I.
2-(4-n-Heptyloxyphenyl)-5-n-octyl-1,3,4-thiadiazole K 70 $S_C$ 85 I.
2-(4-n-Nonyloxyphenyl)-5-n-heptyl-1,3,4-thiadiazole K 72 $S_C$ 87 I.
2-[4-(4-Methylpentyl)-phenyl]-5-(4'-n-hexyloxyphenyl)-1,3,4-thiadiazole K 89 $S_C$ 154 N 169 I.
2-[4-(4-Methylpentyl)-phenyl]-5-(4'-n-heptyloxyphenyl)-1,3,4-thiadiazole K 89 $S_C$ 156 N 165 I.
2-[4-(4-Methylbutyl)-phenyl]-5-(4'-n-decylphenyl)-1,3,4-thiadiazole K 92 $S_C$ 140 N 153.1 I.

Example 65

A liquid-crystalline medium consisting of
3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
5% of 2-p-hexyloxyphenyl-5-nonylpyrimidine,
20% of 2-p-nonyloxyphenyl-5-nonylpyrimidine,
20% of r-1-cyano-cis-4-(4'-octyloxybiphenyl-4-yl)-1-octylcyclohexane,
10% of r-1-cyano-cis-4-(4'-octyloxybiphenyl-4-yl)-1-nonylcyclohexane,
9% of r-1-cyano-cis-4-(4'-heptyloxybiphenyl-4-yl)-1-hexylcyclohexane,
10% of optically active 4-(5-heptylpyrimid-2-yl)-phenyl 2-chloroisovalerate,
4% of 2-(4-n-octyloxyphenyl)-5-n-hexyl-1,3,4-thiadiazole
6% of 2-(4-n-nonyloxyphenyl)-5-n-heptyl-1,3,4-thiadiazole, and
4% of optically active 2-[4-(2-chloroisovaleroyloxy)-phenyl]-5-n-heptyl-1,3,4-thiadiazole
shows $S_C$* 64 $S_A$ 80 Ch 83 I and a spontaneous polarization of 17 nC/cm$^2$ at 20°.

Example 66

3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
3% of 2-p-hexyloxyphenyl-5-nonylpyrimidine,
25% of 2-p-nonyloxyphenyl-5-nonylpyrimidine,
15% of r-1-cyano-cis-4-(4'-octyloxybiphenyl-4-yl)-1-octylcyclohexane,
20% of r-1-cyano-cis-4-(4'-octyloxybiphenyl-4-yl)-1-nonylcyclohexane,
10% of r-1-cyano-cis-4-(4'-heptyloxybiphenyl-4-yl)-1-hexylcyclohexane,
10% of optically active 4-(5-heptylpyrimid-2-yl)-phenyl 2-chloroisovalerate and
5% of optically active 2-[4-(2-methyl-2-cyanoisovaleroyloxy)-phenyl]-5-n-heptyl- 1,3,4-thiadiazole give $S_C^*$ 64 $S_A$ 74 Ch 85 I and a spontaneous polarization of 21 nC/cm² at 20°.

Example 67

A liquid-crystalline phase prepared which consists of:
3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
5% of 2-p-hexyloxyphenyl-5-nonylpyrimidine,
25% of 2-p-nonyloxyphenyl-5-nonylpyrimidine,
28% of r-1-cyano-cis-4-(4'-butyloxybiphenyl-4-yl)-1-octyl-cyclohexane,
14% of r-1-cyano-cis-4-(trans-4-pentylcyclohexyl)-1-(trans-4-pentylcyclohexyl)-cyclohexane,
10% of p-(5-n-octylpyridin-2-yl)-phenyl 3-methyl-2-chloropentanoate and
5% of 2-(4-n-octyloxyphenyl)-5-(4'-n-heptylphenyl)-1,3,4-thiadiazole.

Example 68

2% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
6% of 2-p-hexyloxyphenyl-5-nonylpyrimidine,
22% of 2-p-nonyloxyphenyl-5-nonylpyrimidine,
15% of r-1-cyano-cis-4-(4'-octyloxybiphenyl-4-yl)-1-octyl-cyclohexane,
8% of 2-p-heptyloxyphenyl-5-nonylpyridine,
5% of 2-(4-n-octyloxyphenyl)-5-n-heptyl-1,3,4-thiadiazole,
5% of 2-(4-n-hexyloxyphenyl)-5-n-octyl-1,3,4-thiadiazole,
10% of optically active 4-(5-heptylpyrimid-2-yl)-phenyl 2-chloroisovalerate,
9% of 2-(4-n-pentyloxy)-5-(4'-n-octylphenyl)-1,3,4-thiadiazole and
9% of 2-(3-n-heptyloxy)-5-(4'-n-octylphenyl)-1,3,4-thiadiazole
give $S_C^*$ 78 $S_A$ 84 Ch 95 I and a switching time of 75 μs at room temperature.

Example 69

5% of 2-p-hexyloxyphenyl-5-heptylpyrimidine,
5% of 2-p-heptyloxyphenyl-5-heptylpyrimidine,
5% of 2-p-octyloxyphenyl-5-heptylpyrimidine,
5% of 2-p-nonyloxyphenyl-5-heptylpyrimidine,
6% of 2-p-hexyloxyphenyl-5-nonylpyrimidine,
22% of 2-p-nonyloxyphenyl-5-nonylpyrimidine,
10% of optically active 4-(5-heptylpyrimid-2-yl)-phenyl 2-chloroisovalerate,
9% of 2-(4-n-hexyloxyphenyl)-5-(4'-n-octytphenyl)-1,3,4-thiadiazole,
9% of 2-(4-n-octyloxyphenyl)-5-(4'-n-heptylphenyl)-1,3,4-thiadiazole,
12% of 2-(4-n-pentyloxy)-5-(4'-n-octylphenyl)-1,3,4-thiadiazole and
12% of 2-(4-n-heptyloxy)-5-(4'-n-octylphenyl)-1,3,4-thiadiazole
give $S_C^*$ 68 $S_A$ 85 I and a switching time of 30 μs at room temperature.

Example 70

5% of 2-p-hexyloxyphenyl-5-heptylpyrimidine,
5% of 2-p-heptyloxy phenyl-5-heptylpyrimidine,
5% of 2-p-octyloxyphenyl-5-heptylpyrimidine,
5% of 2-p-nonyloxyphenyl-5-heptylpyrimidine,
7% of 2-p-hexyloxyphenyl-5-nonylpyrimidine,
24% of 2-p-nonyloxyphenyl-5-nonylpyrimidine,
9% of 2-p-heptyloxyphenyl-5-nonylpyrimidine,
8% of 2-p-octyloxyphenyl-5-nonylpyrimidine,
10% of r-1-cyano-cis-4-(4'-octyloxybiphenyl-4-yl)-1-octyl-cyclohexane,
10% of optically active 4-(5-heptylpyrimid-2-yl)-phenyl 2-chloroisovalerate,
6% of 2-(4-n-pentyloxyphenyl)-5-(4'-n-octylphenyl)-1,3,4-thiadiazole and
6% of 2-(4-n-heptyloxyphenyl)-5-(4'-n-octylphenyl)-1,3,4-thiadiazole
give $S_C^*$ 65 $S_A$ 74 Ch 83 I and a switching time of 50 μs at room temperature.

Example 71

4% of 2-p-hexyloxyphenyl-5-heptylpyrimidine,
4% of 2-p-heptyloxyphenyl-5-heptylpyrimidine,
4% of 2-p-octyloxyphenyl-5-heptylpyrimidine,
5% of 2-p-nonyloxyphenyl-5-heptylpyrimidine,
7% of 2-p-hexyloxyphenyl-5-nonylpyrimidine,
24% of 2-p-nonyloxyphenyl-5-nonylpyrimidine,
4% of 2-p-heptyloxyphenyl-5-nonylpyrimidine,
5% of 2-p-octyloxyphenyl-5-nonylpyrimidine,
9% of r-1-cyano-cis-(4'-octyloxybiphenyl-4-yl)-1-octylcyclohexane,
16% of optically active 4-(5-heptylpyrimid-2-yl)-phenyl 2-chloroisovalerate,
9% of 2-(4-n-pentyloxyphenyl)-5-(4'-n-octylphenyl)-1,3,4-thiadiazole,
9% of 2-(4-n-heptyloxyphenyl)-5-(4'-n-octylphenyl)-1,3,4-thiadiazole and
1% of optically active 2-p-(2,6-dimethylheptyloxy)-phenyl-5-nonylpyrimidine
give K 20 $S_C^*$ 62 $S_A^*$ 77 Ch 95 I.

Example 72

With exclusion of moisture, 0.1 mol of dicyclohexylcarbodiimide in dichloromethane is added to a mixture of 0.1 mol of 2-heptyl-5-p-hydroxyphenyl-1,3,4-thiadiazole and 0.1 mol of optically active 2-methyl-2-butylcyanoacetic acid in 200 mL of dichloromethane, while cooling with ice. The mixture is stirred for a further 12 hours at room temperature, the dicyclohexyl urea is filtered off and 2-[4-(2-cyano-2-methylhexanoyloxy)-phenyl]-5-n-heptyl-1,3,4-thiadiazole is isolated by working up in the usual way.

Example 73

13.3 g of optically active 2-methyl-2-butylcyanoacetyl chloride are added to 18.1 g of p-heptyloxybenzoic acid hydrazide in 150 ml of pyridine and the mixture is stirred for about 12 hours at room temperature. The reaction mixture is then poured into water and extracted with dichloromethane, and the reaction product is isolated by evaporation and recrystallization from toluene/hexane.

11.2 g of the product thus obtained are boiled under reflux for 3 hours together with 12.1 g of Lawesson's reagent in 150 mL of THF. The mixture is then stirred into aqueous sodium hydroxide solution. Working-up of the organic phase in the usual way gives 2-(1-cyano-1-methylpentyl)-5-(4-hexyloxyphenyl)-1,3,4-thiadiazole.

Example 74

8% of 4'-n-heptyloxyphenyl 4-n-octyloxybenzoate,

10% of 4'-n-octyloxyphenyl 4-n-octyloxybenzoate,
12% of 4'-n-nonyloxyphenyl 4-n-octyloxybenzoate,
7% of 4'-n-hexyloxyphenyl 4-n-decyloxybenzoate,
9% of 4'-n-heptyloxyphenyl 4-n-decyloxybenzoate,
11% of 4'-n-octyloxyphenyl 4-n-decyloxybenzoate,
7% of 2-(4-n-decyloxyphenyl)-5-n-heptyl-1,3,4-thiadiazole,
7% of 2-(4-n-decyloxyphenyl)-5-n-nonyl-1,3,4-thiadiazole,
9% of 2-(4-n-octyloxyphenyl)-5-n-(4'-n-pentylphenyl)-1,3,4-thiadiazole,
8% of 2-(4-n-octyloxyphenyl)-5-n-(4'-n-heptylphenyl)-1,3,4-thiadiazole and
12% of optically active 4-(5-heptylpyrimid-2-yl)-phenyl 2-chloroisovalerate
give $S_C^*$ 62 $S_A$ 66 Ch 76 I and a spontaneous polarization of 14 nC×cm$^{-2}$ at 20° C.

Example 75

8% of 4'-octyloxyphenyl 4-n-octyloxybenzoate,
11% of 4'-nonyloxyphenyl 4-n-octyloxybenzoate,
10% of 4'-heptyloxyphenyl 4-n-decyloxybenzoate,
12% of 4'-octyloxyphenyl 4-n-decyloxybenzoate,
8% of 2-p-hexyloxyphenyl-5-octylpyrimidine,
10% of 2-p-heptyloxyphenyl-5-octylpyrimidine,
12% of 2-p-octyloxyphyenyl-5-octylpyrimidine,
9% of 2-(4-n-octyloxyphenyl)-5-(4'-n-pentylphenyl)-1,3,4-thiadiazole,
9% of 2-(4-n-decyloxyphenyl)-5-(4'-n-pentylphenyl)-1,2,4-thiadiazole and
10% of optically active 4-(5-heptylpyrimid-2-yl)-phenyl 2-chloroisovalerate
give $S_C^*$ 60 $S_A$ 68 Ch 74 I and a spontaneous polarization of 12 nC×cm$^{-2}$ at 20° C.

Example 76

3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-hexyloxyphenyl-5-nonylpyrimidine,
23% of 2-p-nonyloxyphenyl-5-nonylpyrimidine,
28% of r-1-cyano-cis-4-(4'-butyloxybiphenyl-4-yl)-1-octyl-cyclohexane,
6% of r-1-cyano-cis-4-(trans-4-pentylcyclohexyl)-1-(trans-4-pentylcyclohexyl)-cyclohexane,
14% of r-1-cyano-cis-4-(4'-heptylbiphenyl-4-yl)-1-hexylcyclohexane and
10% of 2-[4-(2-methyl-2-cyanohexanoytoxy)phenyl]-5-n-heptyl-1,3,4-thiadiazole
give $S_C^*$ 63 $S_A$ 71 Ch 86 I and a spontaneous polarization of 24 nC×cm$^{-2}$ at 20° C.

Example 77

3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
23% of 2-p-nonyloxyphenyl-5-nonylpyrimidine,
28% of r-1-cyano-cis-4-(4'-butyloxybiphenyl-4-yl)-1-octyl-cyclohexane,
6% of r-1-cyano-cis-4-(trans-4-pentylcyclohexyl)-1-(trans-4-pentylcyclohexyl)-cyclohexane,
14% of r-1-cyano-cis-4-(4'-heptylbiphenyl-4-yl)-1-hexylcyclohexane and
10% of 2-[4-(2-hexyloxyphenyl)-5-(2-methyl-2-cyanopentyl)-1,3,4-thiadiazole
give $S_C^*$ 45 $S_A$ 64 Ch 83 I and a spontaneous polarization of 16 nC×cm$^{-2}$ at 20° C.

We claim:

1. A medium for use in a ferroelectric liquid crystal cell, said medium having a tilted smectic liquid-crystalline phase and comprising 3–15 compounds, wherein at least one of said compounds is a liquid-crystal compound which exhibits a $S_c$ phase and contains one 1,3,4-thiadiazole-2,5-diyl ring and does not exhibit a 2-chloro-3-methylbutyryloxy wing group; and said 3–15 compounds all exhibit wing groups other than H atoms attached to the terminal ring groups.

2. A medium according to claim 1, wherein said medium contains a component having a negative dielectric anisotropy.

3. A medium according to claim 1, wherein said medium further contains at least one compound of the formula IIa

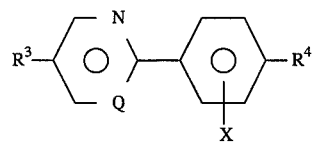

wherein $R^3$ and $R^4$ each independently of one another are alkyl or alkoxy having 5 to 12 C atoms, Q is CH or N and X is H or F.

4. A medium according to claim 3, wherein Q is N and X is H.

5. A medium according to claim 3, wherein $R^3$ and $R^4$ are straight-chain alkyl.

6. A medium according to claim 3, wherein said medium contains 35 to 75% of phenylpyridines.

7. A medium according to claim 1 wherein said medium further contains at least one compound of the formula IIb

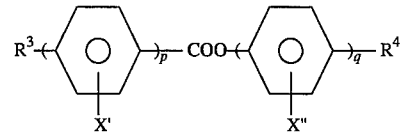

wherein $R^3$ and $R^4$ each independently of one another are alkyl or alkoxy having 5 to 12 C atoms, X' and X" each independently of one another are H or F and p and q are each 1 or 2, with the proviso that (p+q) is 2 or 3.

8. A medium according to claim 7, wherein $R^3$ and $R^4$ are straight-chain alkyl or alkoxy groups.

9. A medium according to claim 7, wherein said medium contains 10 to 75% of at least one compound of formula IIb.

10. In a electro-optical display element, comprising a ferroelectric liquid crystal cell, the improvement comprising said cell containing a liquid-crystalline medium according to claim 1 as a dielectric.

11. A medium according to claim 1, wherein said compound which exhibits a $S_c$ phase is of the formula

wherein p is 0 or 1, one of the groups $R^1$ and $R^2$ is

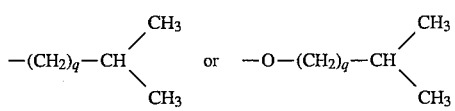

in which q can be 2 to 7, and the other of the groups $R^1$ and $R^2$ is straight-chain alkyl or alkoxy having 3 to 12 C atoms.

12. A method according to claim 11, wherein q is 3.

13. In a liquid-crystal display containing a liquid-crystal medium, the improvement wherein said medium is one of claim 4.

14. A medium according to claim 1, wherein said medium contains at least one compound of the formula IIa

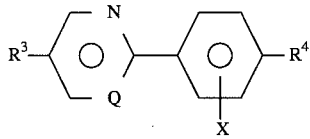

wherein $R^3$ and $R^4$ each independently of one another are alkyl or alkoxy having 5 to 12 C atoms, Q is CH or N and X is H or F.

15. In a liquid-crystal display containing a liquid-crystal medium, the improvement wherein said medium is one of claim 14.

16. A medium according to claim 1, wherein said medium contains at least one thiadiazole compound of the formula

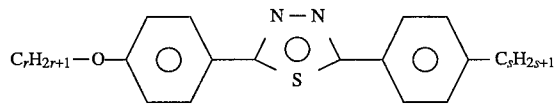

wherein r is 8, 9 or 10 and s is 5, 6, 7, 8, 9, 11 or 12.

17. A medium according to claim 1, wherein said liquid-crystal compound which exhibits a $S_c$ phase is of the formula I $$R^1-A^1-Z^1-A^2-(Z^2-A^3)_n-R^2 \qquad (I)$$

wherein one of the rings $A^1$, $A^2$ and $A^3$ is 1,3,4-thiadiazole-2,5-diyl $A^1$, $A^2$ and $A^3$ otherwise are each independently of one another a 1,4-phenylene group which is unsubstituted or mono- or poly-substituted by halogen, nitrile and/or alkyl and in which one or more CH groups can also be replaced by N, a 1,4-cyclohexylene group which is unsubstituted or CN-substituted and in which one or two non-adjacent $CH_2$ groups can each also be replaced by O or S, or one of the groups 1,4-bicyclo(2,2,2)octylene, piperidine- 1,4-diyl, naphthalene-2,6-diyl, decahydronaphthalene-2,6-diyl or 1,2,3,4-tetrahydronaphthalene-2,6-diyl;

$R^1$ and $R^2$ are each independently of one another an alkyl group having 1–15 C atoms or a $C_{1-15}$-alkyl wherein one or more $CH_2$ groups are each replaced by one of the radicals —O—, —S—, —CO—, —O—CO—, —CO—O—, —CO—S—, —S—CO—, —CH(halogen)—, —$CF_2$—, —CHCN—, —C(alkyl)CN—, —CH=CH—, or —C≡C— and, optionally having an asymmetric carbon atom causing optical activity, and one of the radicals $R^1$ and $R^2$ can also be F, Cl, Br, CN, COOH, OH, SH, $NH_2$, $NO_2$ or —NCS, and $R^1$ and $R^2$ are not 2-chloro-3-methylbutyryloxy;

$Z^1$ and $Z^2$ are each independently of one another —CO—O—, —O—CO—, —$CH_2CH_2$—, —$CH_2$—O—, —$OCH_2$—, —N=N—, —NO=N—, —CH=N—, or a single bond, and one of the groups $Z^1$ and $Z^2$ can also be —$CH_2$—, —O—, —CO—, —CHCN—, —CH(halogen)—, —$CH_2CH_2CH_2$—, —$CH_2$—COO— or —$CH_2OCO$—; and n is 0, 1, 2, or 3;

wherein at least one of $R^1$ and $R^2$ is an optically active organic radical of the formula

—X—Q—*CHCN—R, wherein

X is —CO—O—, —O—CO—, —O—CO—O—, —CO—, —S—, —CH=CH—, —CH=CH—COO— or a single bond;

Q is alkylene having 1 to 5 C atoms, wherein a $CH_2$ group not linked to X can also be replaced by —O—, —CO—, —O—CO—, —CO—O— or —CH=CH—, or a single bond; and R is H or an alkyl or alkoxy group which has 1 to 18 C atoms and in which one or two non-adjacent $CH_2$ groups can also be replaced by —O—, —CO—, —O—CO—, —CO—O— and/or —CH=CH—.

18. A medium according to claim 1, wherein said medium contains at least one thiadiazole compound of the formula

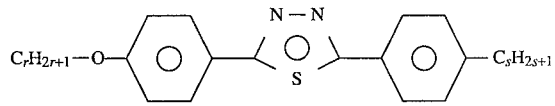

wherein r is 8 or 9 and s is 5, 6, 7, 8, 9, 10, 11, or 12.

19. A medium according to claim 1, wherein said medium contains at least one compound of the formula alkoxy-Phe-A-alkyl, wherein alkoxy is straight chain decyloxy, alkyl is straight chain pentyl, hexyl, heptyl, octyl, nonyl, or decyl, and A is 1,3,4-thiadiazole-2,5-diyl.

20. A medium according to claim 1, wherein said medium contains at least one compound of the formula alkoxy-Phe-A-alkyl, wherein alkoxy is straight chain pentoxy, hexoxy, heptoxy, octoxy, nonoxy, or decyloxy, alkyl is straight chain octyl, nonyl, or decyl, and A is 1,3,4-thiadiazole-2,5-diyl.

21. A medium according to claim 1, wherein said medium contains at least one compound of the formula alkyl-Phe-A-alkyl, wherein alkyl is straight-chain pently, hexyl, heptyl, octyl, nonyl, or decyl an A is 1,3,4-thiadiazole-2,5-diyl.

22. A medium for use in a ferroelectric liquid crystal cell, said medium having a tilted smectic liquid-crystalline phase and comprising at least two compounds, wherein at least one of said compounds is a liquid-crystal compound which exhibits a $S_c$ phase and contains one 1,3,4-thiadiazole-2,5-diyl ring, said compound being of the formula:

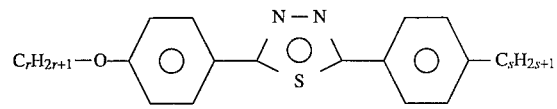

wherein r is 8 or 9 and s is 5, 6, 7, 8, 9, 10, 11 or 12.

23. A medium for use in a ferroelectric liquid crystal cell, said medium having a tilted smectic liquid-crystalline phase and comprising at least two compounds, wherein at least one of said compounds is a liquid-crystal compound which exhibits a $S_c$ phase and contains one 1,3,4-thiadiazole-2,5-diyl ring, said compound being of the formula:

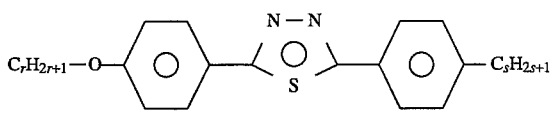

wherein r is 6 and s is 5, 6, 7, 8, 9, 10, 11 or 12.

24. A medium for use in a ferroelectric liquid crystal cell, said medium having a tilted smectic liquid-crystalline phase and comprising 3–15 compounds, wherein at least one of said compounds is a liquid-crystal compound which exhibits a $S_c$ phase and contains one 1,3,4-thiadiazole-2,5-diyl ring, said compound being of the formula:

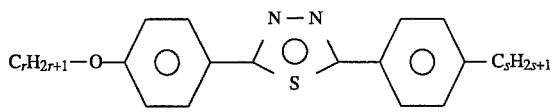

wherein r is 10 and s is 5, 6, 7, 8, 9, 11 or 12; and said 3–15 compounds all exhibit wing groups other than H atoms attached to the terminal ring groups.

25. A medium according to claim 22, wherein groups $C_rH_{2r+1}$ and $C_sH_{2s+1}$ are straight-chain alkyl groups.

26. A medium according to claim 22, wherein r and s are selected as follows:

| r | 8 8 8 8 8 | 9 9 9 9 9 |
|---|-----------|-----------|
| s | 5 7 8 9 10 | 5 7 8 9 10 |

27. A medium according to claim 23, wherein groups $C_rH_{2r+1}$ and $C_sH_{2s+1}$ are straight-chain alkyl groups.

28. A medium according to claim 23, wherein s is 5, 7, 8, 9 or 10.

* * * * *